(12) United States Patent
Pezzotta

(10) Patent No.: US 11,833,733 B2
(45) Date of Patent: Dec. 5, 2023

(54) METHOD AND APPARATUS FOR PRODUCING ELASTIC LAMINATES

(71) Applicant: Fameccanica.Data S.p.A., San Giovanni Teatino (IT)

(72) Inventor: Vincenzo Pezzotta, San Giovanni Teatino (IT)

(73) Assignee: Fameccanica.Data S.p.A., San Giovanni Teatino (IT)

(*) Notice: Subject to any disclaimer, the term of this patent is extended or adjusted under 35 U.S.C. 154(b) by 330 days.

(21) Appl. No.: 17/363,150

(22) Filed: Jun. 30, 2021

(65) Prior Publication Data
US 2022/0001592 A1 Jan. 6, 2022

(30) Foreign Application Priority Data
Jul. 1, 2020 (IT) .................. 102020000015871

(51) Int. Cl.
| | | |
|---|---|---|
| B29C 55/08 | (2006.01) | |
| B32B 5/02 | (2006.01) | |
| B32B 25/10 | (2006.01) | |
| B32B 38/00 | (2006.01) | |
| A61F 13/15 | (2006.01) | |

(52) U.S. Cl.
CPC .............. B29C 55/08 (2013.01); B32B 5/022 (2013.01); B32B 25/10 (2013.01); B32B 38/0004 (2013.01); B32B 38/0012 (2013.01); A61F 13/15699 (2013.01); *B29C 2793/0036* (2013.01); *B32B 2038/0028* (2013.01); *B32B 2555/02* (2013.01)

(58) Field of Classification Search
CPC . B29C 55/08; B29C 2793/0036; B32B 5/022; B32B 25/10; B32B 38/0004; B32B 38/0012; B32B 38/18; B32B 3/18; B32B 2038/0028; B32B 2555/02; A61F 13/15699; A61F 13/15
USPC ....................................... 493/339
See application file for complete search history.

(56) References Cited

U.S. PATENT DOCUMENTS

| | | | | |
|---|---|---|---|---|
| 3,819,465 A | * | 6/1974 | Parsons ..................... | B32B 5/26 442/13 |
| 4,556,441 A | * | 12/1985 | Faasse, Jr. .............. | B32B 38/10 156/247 |
| 4,735,673 A | * | 4/1988 | Piron .................. | B32B 37/0076 156/496 |
| 5,376,198 A | * | 12/1994 | Fahrenkrug ....... | A61F 13/15203 156/290 |
| 5,389,168 A | * | 2/1995 | Litchholt ................... | C09J 5/08 264/45.9 |
| 5,834,381 A | * | 11/1998 | Roe ......................... | B32B 5/026 428/68 |

(Continued)

FOREIGN PATENT DOCUMENTS

EP 3496687 A1 6/2019

OTHER PUBLICATIONS

Italian Search Report dated Mar. 4, 2021. 8 pages.

*Primary Examiner* — Dariush Seif
(74) *Attorney, Agent, or Firm* — RMCK Law Group PLC

(57) ABSTRACT

A method and apparatus for producing elastic laminates wherein a first and a second elastic film are stretched in the transverse direction by respective spreader devices, and are applied on a transfer wheel which—in turn—applies the first and second elastic films on a non-woven web held on the outer cylindrical surface of an anvil wheel.

10 Claims, 3 Drawing Sheets

(56) References Cited

U.S. PATENT DOCUMENTS

| | | | | |
|---|---|---|---|---|
| 6,273,984 B1* | 8/2001 | Bourdelais | ......... | B32B 37/0015 430/935 |
| 6,506,473 B1* | 1/2003 | Hisanaka | ............. | A61F 13/512 428/137 |
| 6,821,370 B2* | 11/2004 | Tomsovic | ......... | A61F 13/15764 156/200 |
| 8,557,077 B2* | 10/2013 | Coose | ............. | A61F 13/15804 156/265 |
| 9,498,941 B2* | 11/2016 | Sablone | ........... | A61F 13/15593 |
| 10,561,537 B2* | 2/2020 | Lenser | ............. | A61F 13/15601 |
| 10,568,775 B2* | 2/2020 | Lenser | ............. | A61F 13/49019 |
| 10,568,776 B2* | 2/2020 | Lenser | ............. | B29C 66/83413 |
| 10,575,993 B2* | 3/2020 | Lenser | ............. | A61F 13/15593 |
| 10,828,204 B2* | 11/2020 | Nelson | ............. | A61F 13/15764 |
| 10,959,887 B2* | 3/2021 | Lenser | ............. | B29C 66/00145 |
| 10,966,876 B2* | 4/2021 | Lenser | ............. | A61F 13/15674 |
| 11,071,654 B2* | 7/2021 | Lenser | ..................... | B32B 7/05 |
| 11,083,633 B2* | 8/2021 | Lenser | ............. | A61F 13/49019 |
| 11,266,543 B2* | 3/2022 | Lenser | ............. | A61F 13/15723 |
| 11,331,223 B2* | 5/2022 | Lenser | ............. | B29C 66/00145 |
| 11,382,798 B2* | 7/2022 | Lenser | ..................... | B32B 7/05 |
| 11,596,557 B2* | 3/2023 | Lenser | ................... | B29C 65/08 |
| 11,617,687 B2* | 4/2023 | Lenser | ............. | B29C 66/83413 156/73.1 |
| 11,642,250 B2* | 5/2023 | Lenser | ............. | A61F 13/49019 156/73.1 |
| 2003/0089447 A1* | 5/2003 | Molee | ................... | B32B 3/085 428/114 |
| 2003/0124331 A1* | 7/2003 | Morell | ................ | B32B 27/02 428/176 |
| 2003/0150551 A1* | 8/2003 | Baker | ............... | A61F 13/15723 156/519 |
| 2004/0005835 A1* | 1/2004 | Zhou | ..................... | B32B 37/144 442/329 |
| 2004/0121683 A1* | 6/2004 | Jordan | ................ | B32B 5/08 442/268 |
| 2006/0147716 A1* | 7/2006 | Braverman | ............. | B32B 27/32 156/244.11 |
| 2006/0162843 A1* | 7/2006 | Baldauf | .................. | B32B 5/142 156/229 |
| 2006/0254708 A1* | 11/2006 | Wada | ................ | A61F 13/15699 156/271 |
| 2007/0044608 A1* | 3/2007 | Franke | .............. | A61F 13/15682 83/39 |
| 2009/0306617 A1* | 12/2009 | Tsang | ................ | A61F 13/49012 604/385.24 |
| 2010/0062231 A1* | 3/2010 | Abed | ....................... | B32B 5/04 156/244.11 |
| 2011/0155301 A1* | 6/2011 | Gilgenbach | ....... | A61F 13/15804 156/163 |
| 2012/0037300 A1* | 2/2012 | Bader | ................... | A61F 13/622 156/244.11 |
| 2012/0159753 A1* | 6/2012 | Andrews | ................. | A61F 13/15 26/70 |
| 2013/0149925 A1* | 6/2013 | Handziak | ............ | B29C 66/1122 442/1 |
| 2014/0041786 A1* | 2/2014 | Henke | ................... | B32B 37/144 156/164 |
| 2014/0174648 A1* | 6/2014 | Oetjen | ................. | B32B 37/203 156/263 |
| 2015/0173956 A1* | 6/2015 | Coe | ..................... | A61F 13/1565 156/252 |
| 2015/0313774 A1* | 11/2015 | Homoelle | ......... | A61F 13/15593 156/192 |
| 2016/0331600 A1* | 11/2016 | Polidori | ........... | A61F 13/15739 |
| 2016/0332418 A1* | 11/2016 | Jenkins | .................... | B32B 5/26 |
| 2017/0100925 A1* | 4/2017 | Homoelle | ............... | B29C 65/72 |
| 2017/0252229 A1* | 9/2017 | Bonelli | ............ | A61F 13/49014 |
| 2017/0305128 A1* | 10/2017 | Kitzmiller | ............... | B32B 5/022 |
| 2018/0029344 A1* | 2/2018 | Hamm | ..................... | C08F 10/06 |
| 2018/0042778 A1* | 2/2018 | Lenser | ................ | B32B 37/1018 |
| 2018/0042779 A1* | 2/2018 | Lenser | ............. | A61F 13/49012 |
| 2018/0042780 A1* | 2/2018 | Lenser | ............. | A61F 13/49019 |
| 2018/0042787 A1* | 2/2018 | Lenser | ............. | A61F 13/15674 |
| 2018/0333943 A1* | 11/2018 | Middlesworth | ........... | B32B 5/26 |
| 2019/0046363 A1* | 2/2019 | Lenser | ..................... | B32B 7/05 |
| 2019/0117469 A1* | 4/2019 | Kunihiro | ............. | A61F 13/4902 |
| 2019/0118509 A1* | 4/2019 | D'Aponte | ........... | B29C 65/7457 |
| 2020/0170846 A1* | 6/2020 | Lenser | ................ | B32B 37/1018 |
| 2020/0179179 A1* | 6/2020 | Lenser | ............. | A61F 13/15593 |
| 2020/0268563 A1* | 8/2020 | Lenser | ..................... | B29C 66/43 |
| 2021/0085532 A1* | 3/2021 | Lenser | ............. | A61F 13/15609 |
| 2021/0186769 A1* | 6/2021 | Lenser | ............. | A61F 13/15731 |
| 2021/0186770 A1* | 6/2021 | Lenser | ............. | A61F 13/15699 |
| 2021/0307970 A1* | 10/2021 | Lenser | ................... | B32B 5/022 |
| 2021/0330514 A1* | 10/2021 | Lenser | ................... | B29C 65/08 |
| 2021/0378367 A1* | 12/2021 | Gilbert | ............... | A44B 18/0061 |
| 2022/0001592 A1* | 1/2022 | Pezzotta | ................... | B32B 3/02 |
| 2022/0161540 A1* | 5/2022 | Cheng | ................... | B05D 1/265 |
| 2022/0233362 A1* | 7/2022 | Lenser | ............. | A61F 13/15674 |
| 2022/0287887 A1* | 9/2022 | Lenser | ................... | B29C 66/43 |
| 2022/0323272 A1* | 10/2022 | Kunihiro | ............... | B32B 27/302 |
| 2023/0157900 A1* | 5/2023 | Lenser | ................ | B32B 38/0012 156/73.1 |

\* cited by examiner

METHOD AND APPARATUS FOR PRODUCING ELASTIC LAMINATES

CROSS-REFERENCE TO RELATED APPLICATION

This application claims priority to Italian Patent Application No. 102020000015871 filed Jul. 1, 2020. The disclosure of the above application is incorporated herein by reference in its entirety.

FIELD OF THE INVENTION

The present invention relates to a method and an apparatus for producing elastic laminates.

The invention has been developed with particular regard to producing elastic laminates intended to be used for producing absorbent sanitary articles.

DESCRIPTION OF THE PRIOR ART

For producing absorbent sanitary articles, such as diapers and other absorbent articles, components with different properties are assembled together, such as absorbent cores, backsheets, topsheets, elastic waist bands, elastic side panels, closing formations, elastic barriers for the legs (leg cuffs), etc.

Some components of absorbent sanitary articles, such as elastic bands for the legs, elastic leg barriers, elastic side panels, elastic waist bands, etc., are made from elastic laminates.

Elastic laminates can be produced in various ways depending on the characteristics of the absorbent sanitary articles. For example, some types of elastic laminates may be formed from one or more non-woven webs bonded to an elastic film. In certain applications, the elastic film is stretched in a transverse direction before being fixed between two opposite non-woven webs.

EP3496687 describes a method and an apparatus for assembling elastic laminates wherein a first non-woven web is wound on an outer cylindrical surface of an anvil wheel rotating around a rotation axis, a first and a second elastic film are stretched in a transverse direction on a first and a second spreader device, and are applied on the first non-woven web on the anvil wheel in a first and second application zone displaced axially and angularly relative to each other with respect to the axis of rotation, a second non-woven web is fed to the anvil wheel above the first and second elastic film stretched in the transverse direction, and the first and second non-woven web are welded together ultrasonically through the first and second elastic film and in a central portion comprised between the first and second elastic film.

In the solution described in EP3496687, the first and second elastic film stretched in the transverse direction are transferred from the inclined surfaces of the spreading devices to a non-woven web wound on a cylindrical surface. This creates difficulties in positioning the elastic films as it is difficult to accurately transfer the stretched elastic films from an inclined surface to a cylindrical surface on which a non-woven web is wound. In the solution known from this document, the first and second elastic film, stretched in the transversal direction, are applied to the non-woven web in two areas that are angularly offset from each other. This too causes difficulties in positioning the elastic films with respect to the non-woven web and involves problems in ensuring a precise spacing between the two elastic films.

Other similar solutions are described in EP3496688, EP3496689, EP3496690.

OBJECT AND SUMMARY OF THE INVENTION

The present invention aims to provide a method and apparatus for producing elastic laminates that overcome the problems of the prior art.

According to the present invention, this object is achieved by a method and by an apparatus having the features forming the subject of claims 1 and 7.

In the solution according to the present invention, the problems of positioning and aligning the stretched elastic films in the transverse direction with respect to the non-woven web are solved due to the fact that the first and second elastic film stretched in the transverse direction are applied directly in contact with the outer cylindrical surface of a transfer wheel. The non-woven web is wound onto the outer cylindrical surface of an anvil wheel, and the first and second elastic film stretched in the transverse direction are applied by the transfer wheel to the non-woven web wound on the anvil wheel in application zones offset from each other in the axial direction and aligned with each other in the angular direction. This solution has the following advantages:

- the transfer of the elastic films from the inclined surfaces of the spreading devices to the outer cylindrical surface of the transfer wheel takes place without the interposition of the non-woven web; therefore, the positioning of the stretched elastic films in the transverse direction on the outer cylindrical surface of the transfer wheel takes place with greater precision;
- the transfer of the stretched elastic films in the transversal direction from the cylindrical surface of the transfer wheel to the non-woven web wound on the outer cylindrical surface of the anvil wheel is carried out in application zones aligned with each other in an angular direction; this allows obtainment of a more precise positioning between the two stretched elastic films in the transverse direction with respect to the non-woven web;
- the application of stretched elastic films in a transversal direction to the non-woven web takes place between two cylindrical surfaces tangent and with respective rotation axes parallel to each other, and this avoids the difficulties due to the transfer on a non-woven web of elastic films stretched in a transverse direction from inclined surfaces to a cylindrical surface.

The method and the apparatus according to the present invention therefore overcome the problems of the solution described in EP3496687.

BRIEF DESCRIPTION OF THE DRAWINGS

The present invention will now be described in detail with reference to the attached drawings, given purely by way of non-limiting example, wherein.

Figure 1:
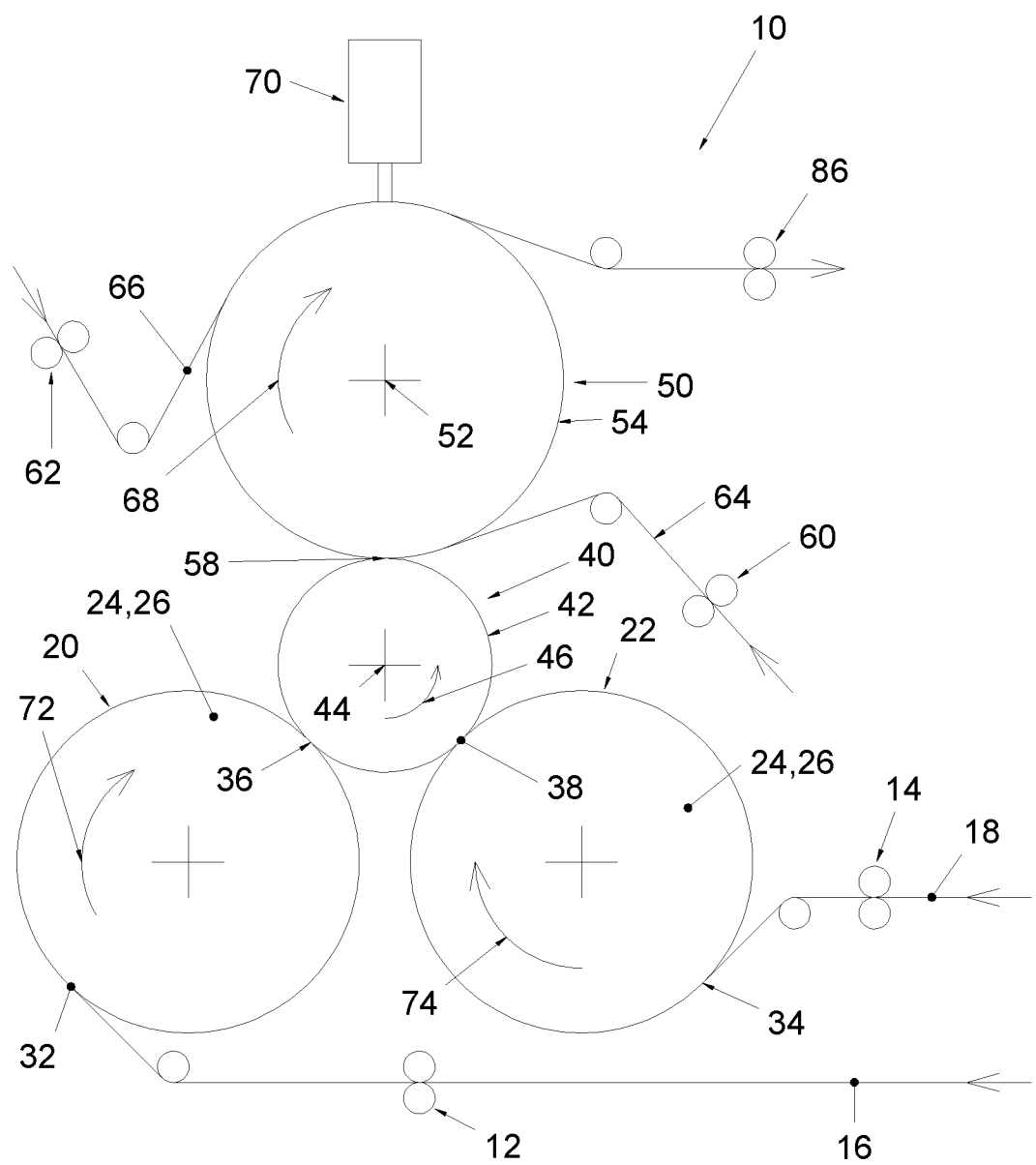
FIG. 1 is a schematic side view of an apparatus according to the present invention.

It will be appreciated that, in the drawings, some components may not be illustrated to simplify the understanding of the figures, and that the various figures may not be represented on the same scale.

DETAILED DESCRIPTION

With reference to FIG. 1, numeral 10 indicates an apparatus for producing elastic laminates.

The apparatus 10 comprises a first feeding device 12 and a second feeding device 14 configured to feed, respectively, a first elastic film 16 and a second elastic film 18 in directions parallel to the respective longitudinal axes.

The apparatus 10 comprises a first spreader device and a second spreader device 22, configured to stretch in a transverse direction the first elastic film 16 and, respectively, the second elastic film 18.

Figure 2:
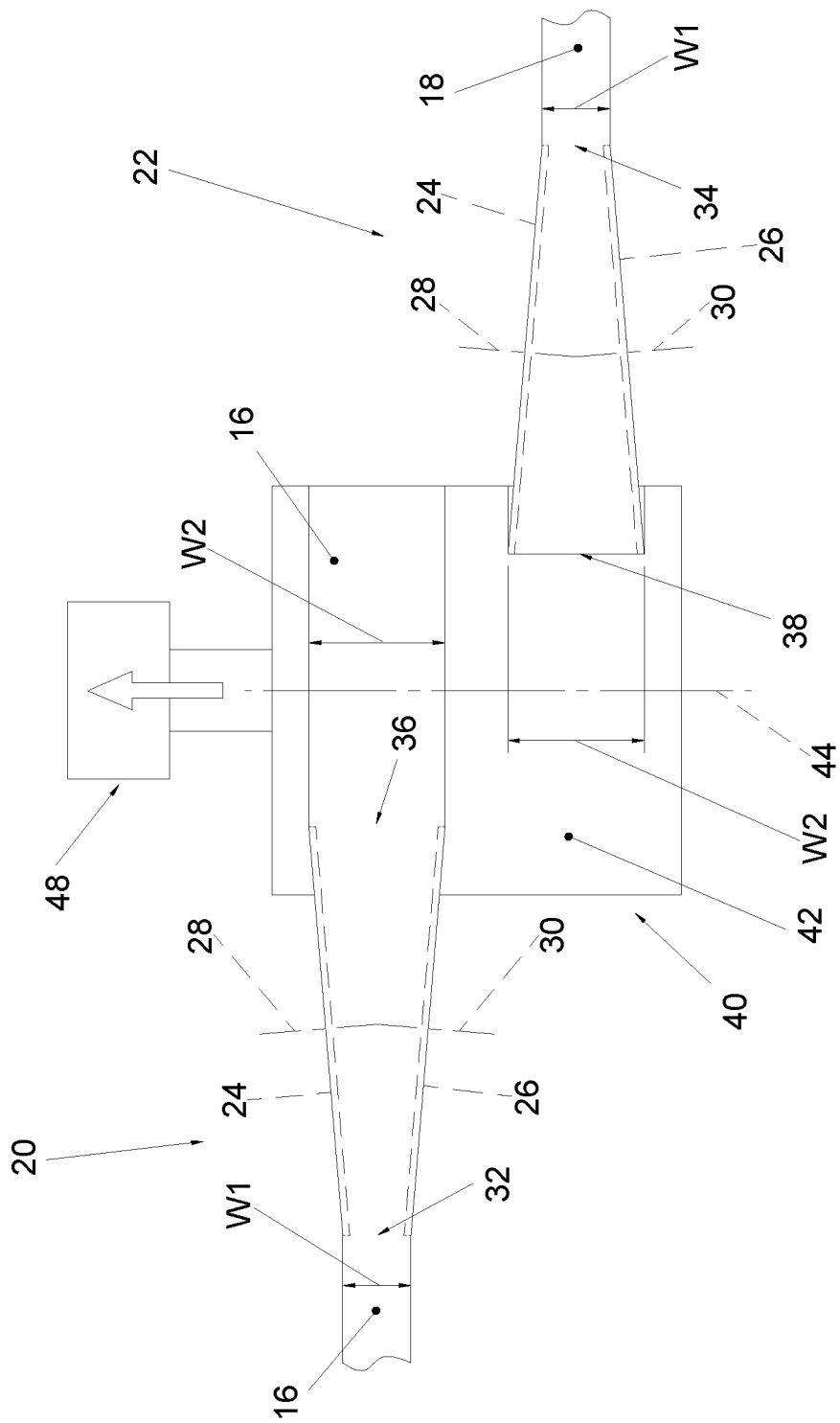
FIGS. 2 and 3 are schematic plan views of two details of the apparatus according to the present invention.

With reference to FIG. 2, each of the two spreading devices 20, 22 comprises two discs 24, 26 rotatable about respective inclined axes 28, 30. The discs 24, 26 have respective circumferential edges provided with means for gripping the elastic films 16, 18. In a possible embodiment, the discs 24, 26 may be provided on their circumferential edges with holes connected to a source of sub-atmospheric pressure for gripping the side edges of the elastic films 16, 18 by suction. The circumferential edges of the discs 24, 26 may also be provided with protruding pins that engage the side edges of the elastic films 16, 18 alternatively or in addition to the vacuum gripping means.

Again with reference to FIG. 2, each spreader device 20, 22 has a respective gripping area 32, 34 and a respective application zone 36, 38. The discs 24, 26 are spaced from each other in the transverse direction by a minimum distance in the gripping areas 32, 34 and by a maximum distance in the application zones 36, 38. The spreader devices 20, 22 pick up the respective elastic films 16, 18 in the respective gripping areas 32, 34 with a first width W1, and release them in the respective application zones 36, 38 with a second width W2. In the path from the gripping areas 32, 34 to the application zones 36, 38, the elastic films 16, 18 are, therefore, elastically stretched in a transverse direction.

In the embodiment illustrated in the figures, the first width W1 and the second width W2 are, respectively, the same for the two elastic films 16, 18. In possible embodiments, the first and second elastic films 16, 18 may have first widths W1 and/or second widths W2, respectively, which are different from each other. In a possible embodiment, the first and second elastic films 16, 18 may have respective first widths W1 that are different from each other before being stretched in the transverse direction. In a possible embodiment, the first and second elastic films 16, 18 after being stretched in the transverse direction may have respective second widths W2 that are different from each other.

With reference to FIGS. 1 and 2, the apparatus 10 comprises a transfer wheel 40 having an outer cylindrical surface 42. The transfer wheel 40 is rotatable about a first axis of rotation 44 in the direction indicated by the arrow 46 in FIG. 1. The outer cylindrical surface 42 of the transfer wheel 40 is provided with holes pneumatically connected to a source of sub-atmospheric pressure 48.

With reference to FIG. 2, the first and second spreader devices 20, 22 apply the respective elastic films 16, 18 on the outer cylindrical surface 42 of the transfer wheel 40 in the respective application zones 36, 38. The application zones 36, 38 are the areas wherein the elastic films 16, 18 stretched in the transversal direction are detached from the discs 24, 26 of the spreading devices 20, 22, and are taken by suitable gripping means, for example, by suction on the outer cylindrical surface 42 of the transfer wheel 40.

The first application zone 36 and the second application zone 38 are displaced axially and angularly with respect to each other with respect to the first axis of rotation 44.

Figure 3:
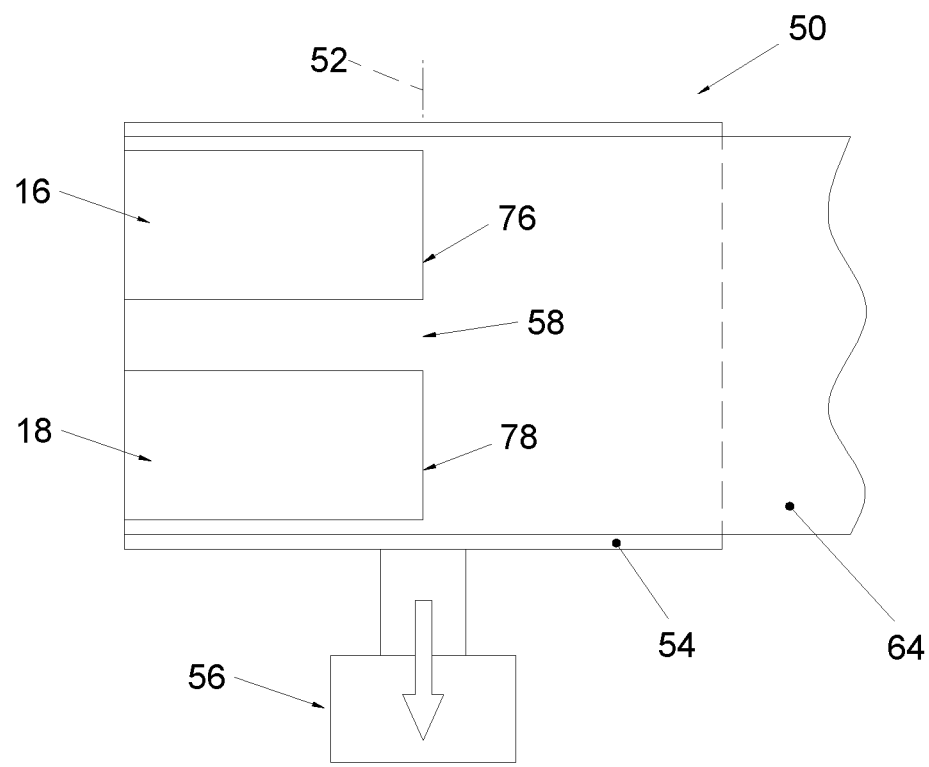

With reference to FIG. 1, the apparatus 10 comprises an anvil wheel 50 rotatable about a second axis of rotation 52 parallel to the first axis of rotation 44 of the transfer wheel 40. The anvil wheel 50 has an outer cylindrical surface 54 provided with holes pneumatically connected to a source of sub-atmospheric pressure 56 (FIG. 3). The outer cylindrical surface 54 of the anvil wheel 50 is tangent to the outer cylindrical surface 42 of the transfer wheel 40 in a transfer zone 58.

The apparatus 10 comprises a third feeding device 60 and a fourth feeding device 62 configured to feed a first non-woven web 64 to the anvil wheel 50 and, respectively, a second non-woven web 66. The first non-woven web 64 is applied to the anvil wheel 50 upstream of the transfer zone 58, or at the transfer area 58, and the second non-woven web 66 is applied to the anvil wheel 50 downstream of the transfer area 58, with reference to the direction of rotation of the anvil wheel 50 indicated by the arrow 68 in FIG. 1.

The apparatus 10 comprises a fastening device 70 cooperating with the outer cylindrical surface 54 of the anvil wheel 50. The fastening device 70 may be an ultrasonic welding device, a pressure device for fastening by adhesive, or a thermal or thermomechanical welding device.

The operation of the apparatus 10 previously described is as follows.

The elastic films 16, 18 may be unwound from respective reels (not illustrated), from respective unwinding devices, and are fed from the respective feeding devices 12, 14 to the respective spreading devices 20, 22. The elastic films 16, 18 may also be obtained by longitudinally cutting a single elastic film unwound from a single reel by a respective unwinding device. The elastic films 16, 18 may be tensioned in the longitudinal direction upstream of the respective spreading devices 20, 22. In the gripping areas 32, 34, the two elastic films 16, 18 are picked up from the discs 24, 26 of the respective spreading devices 20, 22. During the rotation of the discs 24, 26 in the directions indicated by the arrows 72, 74, the elastic films 16, 18 are stretched in the transverse direction. This stretching causes an increase in the width of the elastic films 16, 18 from the value W1 in the gripping areas 32, 34 to the value W2 in the application zones 36, 38 (FIG. 2).

In the application zones 36, 38, the elastic films 16, 18 stretched in the transversal direction detach from the circumferential edges of the discs 24, 26 and are applied directly in contact with the outer cylindrical surface 42 of the transfer wheel 40. The elastic films 16, 18 are kept in a stretched state in a transverse direction on the outer cylindrical surface 42 of the transfer wheel 40 by means of suitable gripping means, for example, by suction. The fact that the elastic films 16, 18 (of non-porous material) are applied directly in contact with the outer cylindrical surface 42 of the transfer wheel 40 without the interposition of a layer of porous material allows retaining the elastic films 16, 18 in a stretched condition in the transverse direction with high relative positioning accuracy.

With reference to FIG. 2, the application zones 36, 38 along which the two elastic films 16, 18 are applied on the outer cylindrical surface 42 of the transfer wheel 40 are displaced both in the axial direction (i.e. in the direction of the axis of rotation of the transfer wheel 40) and in the angular direction (i.e. along an arc of circumference with its center on the rotation axis 44).

The two elastic films 16, 18 on the outer cylindrical surface 42 of the transfer wheel 40 occupy two circumferential bands each with a width W2 that are spaced apart in an axial direction.

With reference to FIGS. 1 and 3, the first non-woven web 64 is applied to the outer cylindrical surface 54 of the anvil wheel 50 upstream of the transfer zone 58.

The first and second elastic films 16, 18, held in a stretched condition in the transverse direction on the transfer wheel 42, are applied onto the first non-woven web 64 held on the outer cylindrical surface 54 of the anvil wheel 50.

With reference to FIG. 3, the first and second elastic films 16, 18 are applied onto the first non-woven web 64 held on the outer cylindrical surface 54 of the anvil wheel 50 in a third application zone 76 and, respectively, in a fourth application zone 78, at the transfer zone 58. The third and fourth application zones 76, 78 are displaced with each other in an axial direction, and are aligned with each other in an angular direction with respect to the axis of rotation 52 of the anvil wheel 50. The third and fourth application zones 76, 78 may have the shape of two lines parallel to the rotation axis 52 and aligned with each other. The fact of applying the first and the second elastic films 16, 18 to the first non-woven web 64 along two application zones 76, 78 aligned with each other in the axial direction ensures a high accuracy of mutual positioning between the two elastic films 16, 18. Furthermore, the fact that transferring the elastic films 16, 18 takes place between two cylindrical surfaces with axes parallel to each other simplifies the transfer of the elastic films, and avoids positioning errors that can occur in the case wherein the elastic films are applied on the non-woven web starting from surfaces with inclined axes as occurs in the solution according to the prior art described in EP3496687.

The elastic films 16, 18 are kept on the anvil wheel in a state tensioned in a transverse direction in contact with the first non-woven web 64 by means of suitable gripping means, for example by suction.

According to the present invention, the gripping means on the discs 24, 26, on the transfer wheel 42 and on the anvil wheel 50 may comprise holes connected to a source of sub-atmospheric pressure for gripping by suction, or protruding pins that engage the side edges of the elastic films 16, 18 alternatively or in addition to the suction means.

After applying the elastic films 16, 18 on the first non-woven web 64 on the outer cylindrical surface 54 of the anvil wheel 50, the second non-woven web 66 is applied on the anvil wheel 50 above the first and the second elastic films 16, 18, so that the two elastic films 16, 18 tensioned in the transverse direction are sandwiched between the first and the second non-woven web 64, 66.

Then, the two non-woven webs 64, 66 are welded together, for example, by ultrasonic welding, through the first and second elastic films 16, 18 by means of the fastening device 70.

According to the present invention, attaching the two non-woven webs 64, 66 to each other through the first and second elastic films 16, 18 includes both the direct fastening of the two webs through an opening in the elastic film, and the fastening of the two webs comprising the elastic film between them. I The fastening device 70 may be configured to form a plurality of connecting points that form respective holes passing through the elastic films 16, 18, and that directly fix the two opposite non-woven webs 64, 66 to each other through the holes formed in the elastic films 16, 18. The elastic films 16, 18 remain anchored to the non-woven webs 64, 66 at the connecting points that extend through the holes formed in the elastic films 16, 18. This solution allows obtainment of breathable elastic laminates thanks to the formation of holes passing through the elastic films 16, 18.

The two non-woven webs 64, 66 may be fixed directly to each other in a central portion comprised between the first and second elastic films 16, 18, and along the longitudinal edges external to the two elastic films 16, 18.

The fastening device 70 may be configured to carry out a uniform fastening pattern over the entire surface of the non-woven webs 64, 66, both at the elastic films 16, 18 and in the areas that do not contain the elastic films 16, 18.

Figure 4:
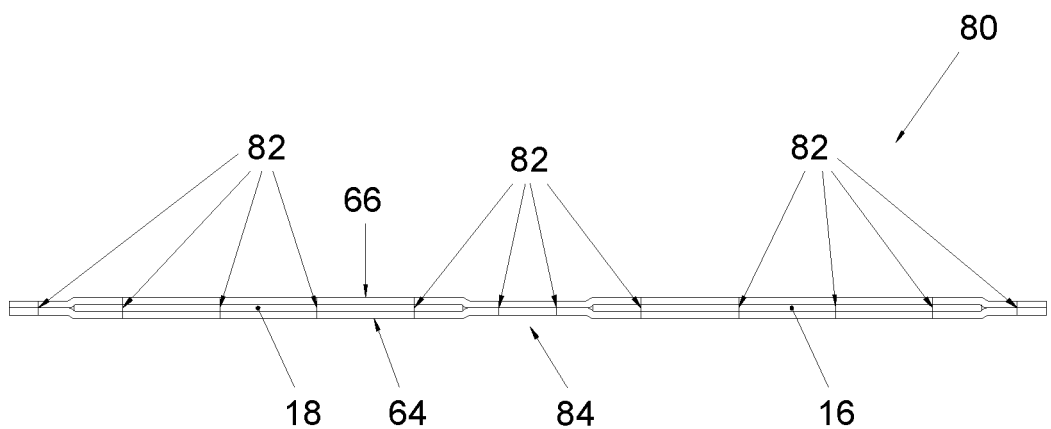
FIG. 4 is a schematic cross-section of an elastic laminate obtained with an apparatus according to the present invention.

Downstream of the fastening device 70, an elastic laminate 80 is obtained having the shape schematically illustrated in FIG. 4, comprising two elastic films 16, 18 enclosed between two non-woven webs 64, 66, and anchored to the two non-woven webs 64, 66 by a pattern of connecting points 82. The elastic laminate 80 has a central portion 84 wherein the two elastic films 16, 18 are spaced apart, and the two non-woven webs 64, 66 are in direct contact with each other.

The central portion 84 of the elastic laminate 80 may be cut in the longitudinal direction by means of a longitudinal cutting device indicated schematically by 86 in FIG. 1. The longitudinal cutting device 86 may carry out a continuous through-cut so as to give rise to two separate elastic sheets, each comprising an elastic film 16, 18 anchored between two non-woven webs 64, 66. In a possible embodiment, the longitudinal cutting device 86 may make a longitudinal weakening line in the central portion 84 of the elastic laminate 80 that constitutes a preferential breaking line, which allows two elastic sheets to be detached from each other following the application of a weak detaching force.

In another embodiment of the present invention, the first non-woven web 64 may be applied to the outer cylindrical surface 54 of the anvil wheel 50 at the transfer zone 58, for example, by first being applied to the transfer wheel 40, above the two elastic films 16, in the stretched state in the transverse direction, between the second application zone 38 and the transfer zone 58.

Of course, without prejudice to the principle of the invention, the details of construction and the embodiments can be widely varied with respect to those described and illustrated, without thereby departing from the scope of the invention as defined by the claims that follow.

The invention claimed is:

1. A method for producing elastic laminates, comprising:
feeding a first and a second elastic film,
stretching the first and second elastic films in a transverse direction on a first and a second spreader device,
applying the first and second elastic films stretched in the transverse direction on an outer circumferential surface of a transfer wheel rotatable around a first axis of rotation, wherein the first and second elastic films are applied onto the outer circumferential surface of the transfer wheel in a first and a second application zone axially and angularly displaced with respect to each other with respect to said first axis of rotation,
applying a first non-woven web on an outer cylindrical surface of an anvil wheel rotatable around a second axis of rotation parallel to the first axis of rotation,
transferring the first and second elastic film from the transfer wheel to the first non-woven web held on the outer cylindrical surface of the anvil wheel in a third and a fourth application zone displaced with respect to each other in an axial direction and angularly aligned with each other with respect to said second axis of rotation, applying a second non-woven web on the anvil wheel above said first and said second elastic films, and forming an elastic laminate by fixing on the anvil wheel the first and second non-woven web through the first and second elastic films.

2. The method according to claim 1, comprising joining to each other the first and the second non-woven web according to a uniform pattern both at the first and second elastic films and in a central portion comprised between said elastic films.

3. The method according to claim 1, comprising cutting in a longitudinal direction a central portion of the elastic laminate comprised between said first and second elastic films.

4. The method according to claim 1, comprising forming a longitudinal weakening line in a central portion of the elastic laminate comprised between said first and second elastic films.

5. The method according to claim 1, comprising transferring the first and second elastic films onto the first non-woven web held on the outer cylindrical surface of the anvil wheel along two application zones in the form of lines parallel to the axis of rotation of the anvil wheel and aligned with each other.

6. The method according to claim 1, wherein the first and second elastic films, after the step of stretching in the transverse direction, have respective second widths that are different from each other.

7. An apparatus for producing elastic laminates, comprising:
- a first and a second feeding device configured to feed a first and a second elastic film,
- a first and a second spreading device configured to stretch the first and second elastic films in a transverse direction,
- a transfer wheel rotatable around a first axis of rotation and having an outer circumferential surface, wherein the first and second spreading devices are configured to apply the first and second elastic films stretched in the transverse direction on the outer circumferential surface of the transfer wheel in a first and a second application zone axially and angularly displaced with respect to each other with respect to said first axis of rotation of the transfer wheel,
- an anvil wheel rotatable around a second axis of rotation parallel to the first axis of rotation, wherein the transfer wheel is tangent to the anvil wheel in a transfer area, and is configured to transfer the first and second elastic film to the anvil wheel in a third and a fourth application zone displaced with respect to each other in an axial direction and aligned with each other in an angular direction with respect to the second axis of rotation of the anvil wheel,
- a third feeding device configured to feed a first non-woven web on an outer cylindrical surface of the anvil wheel upstream of said transfer area, or at said transfer area,
- a fourth feeding device configured to feed a second non-woven web to the anvil wheel downstream of said transfer area, and
- a fixing unit cooperating with the anvil wheel and configured to join to each other the first and second non-woven web through the first and second elastic films.

8. The apparatus according to claim 7, wherein each of said spreader devices comprises a pair of discs rotatable around respective axes inclined to each other.

9. The apparatus according to claim 7, comprising a longitudinal cutting device configured to cut an elastic laminate in a longitudinal direction at an outlet of said anvil wheel.

10. The apparatus according to claim 9, wherein said longitudinal cutting device is configured to form a continuous longitudinal through-cut or a longitudinal weakening line in a central portion of the elastic laminate comprised between the first and second elastic films.

\* \* \* \* \*

UNITED STATES PATENT AND TRADEMARK OFFICE
CERTIFICATE OF CORRECTION

PATENT NO. : 11,833,733 B2
APPLICATION NO. : 17/363150
DATED : December 5, 2023
INVENTOR(S) : Vincenzo Pezzotta Page 1 of 1

It is certified that error appears in the above-identified patent and that said Letters Patent is hereby corrected as shown below:

On the Title Page

(71) Applicant address information should be listed as:
- Fameccanica.Data S.p.A., San Giovanni Teatino (Chieti), ITALY -

(72) Inventor address information should be listed as:
- Vincenzo PEZZOTTA, San Giovanni Teatino (Chieti), ITALY -

(73) Assignee address information should be listed as:
- Fameccanica.Data S.p.A., San Giovanni Teatino (Chieti), ITALY -

Signed and Sealed this
Fourth Day of March, 2025

Coke Morgan Stewart
*Acting Director of the United States Patent and Trademark Office*